United States Patent [19]

Morimoto et al.

[11] Patent Number: 4,958,521
[45] Date of Patent: Sep. 25, 1990

[54] METHOD AND APPARATUS FOR MEASURING A FORCE REQUIRED FOR STRIPPING ADHERED TAPE

[75] Inventors: Kazuhiro Morimoto; Tsuneo Taki, both of Kyoto, Japan

[73] Assignee: Murata Manufacturing Co., Ltd., Japan

[21] Appl. No.: 445,751

[22] Filed: Dec. 4, 1989

[30] Foreign Application Priority Data

Dec. 5, 1988 [JP] Japan .................. 63-307641

[51] Int. Cl.$^5$ .............................. G01N 3/08
[52] U.S. Cl. .................... 73/827; 73/150 A
[58] Field of Search ............ 73/827, 150 A, 842

[56] References Cited
U.S. PATENT DOCUMENTS
3,396,578 8/1968 Skundberg .............. 73/827 X FOREIGN PATENT DOCUMENTS
1536864 12/1978 United Kingdom ............ 73/827

Primary Examiner—Jerry W. Myracle
Attorney, Agent, or Firm—Ostrolenk, Faber, Gerb & Soffen

[57] ABSTRACT

A cover tape is adhered to a receiving tape which is provided with a plurality of cavities distributed for receiving components, to close the openings of the cavities. In order to measure the force required for stripping the cover tape from the receiving tape, the cover tape is bent to be at a prescribed stripping angle from a longitudinal end thereof to be stripped from the receiving tape, and the cover tape and the receiving tape are moved to be separated at the same speed from each other along loci of linear movement respectively while retaining the stripping angle. Tensile force acting on the cover tape is measured during such movement, thereby determining the force required for stripping the cover tape.

26 Claims, 3 Drawing Sheets

METHOD AND APPARATUS FOR MEASURING A FORCE REQUIRED FOR STRIPPING ADHERED TAPE

BACKGROUND OF THE INVENTION

1. Field of the Invention

The present invention relates to a method and an apparatus for measuring a force required for stripping a cover tape which is adhered to a receiving tape in a tape package which contains small components such as chip components.

2. Description of the Background Art

U.S. Pat. No. 4,298,120 granted to Kaneko et al. discloses a tape package containing chip-type electronic components. This tape package comprises a receiving tape which is provided with a plurality of cavities distributed along its longitudinal direction for receiving the components, and a cover tape which is adhered to the receiving tape for closing the cavities receiving the components. The receiving tape is generally prepared from a cardboard material, and the cavities are provided by perforations defined in such a cardboard material. Thus, the cavities form openings on both surfaces of the receiving tape such that first ones of the openings are closed by a bottom tape which is adhered to the receiving tape while second ones are closed by the cover tape after the components are received in the cavities. The cover tape is formed by a sheet which is prepared from thermoplastic resin, for example, and adhered to the receiving tape by a heat seal method on both side edges thereof.

In such a conventional tape package, it is necessary to properly set the force required for stripping the cover tape, giving due consideration to secure maintenance of the packed components and operability of the process of extracting the packed components. To this end, it is suitable to extract a number of samples to measure the force required for stripping the cover tape.

Japanese Patent Laying-Open No. 196645/1985 entitled "Method of Measuring Force for Stripping Adhered Tape and Apparatus Therefor" proposes a method and an apparatus for automatically measuring such force for stripping an adhered tape.

According to this method, a cover tape is stripped at a prescribed stripping angle from an end of a linearly held tape package and the forward end of the cover tape is moved at a constant speed along a locus of linear movement which is at an angle half the stripping angle with, respect to the tape package, thereby to measure the tensile force acting on the forward end of the cover tape.

In the above method, however, it is necessary to cut off a part of the tape package which is wound on a reel or the like, and fix the overall stub to a support, which is a with troublesome operation. Further, the stub must be securely fixed to the support so that the same is not upwardly separated from the support to vary the stripping angle. Consequently, it takes time to replace the stub.

In addition, it is necessary to change the angle of the support as well as to horizontally move the support itself in order to change the stripping angle of the cover tape. Thus, a plurality of portions must be adjusted, which again is a troublesome operation.

SUMMARY OF THE INVENTION

Accordingly, an object of the present invention is to provide a method and an apparatus for measuring the force required for stripping an adhered tape, which method and apparatus have excellent operability for measurement of the stripping force and are capable of easily changing a stripping angle which is involved in the measurement.

The present invention provides a method of measuring the force required for stripping a second tape, which is adhered to a first tape, from the first tape. First, the second tape is bent so that a longitudinal end thereof is at a prescribed stripping angle with respect to the first tape. Then, a portion of the first tape released from the second tape and a portion of the second tape stripped from the first tape are moved in opposite direction from each other at the same speed along loci of linear movement while retaining the said stripping angle. During such movement, the tensile force acting on the second tape is measured in order to determine the force required for stripping the second tape from the first tape.

The inventive method of measurement is preferably adapted to measure the force which is required for stripping a cover tape from a receiving tape. A tape package comprises the receiving tape which is provided with a plurality of cavities distributed along its longitudinal direction for receiving components, and the cover tape which is adhered to the receiving tape for closing the cavities. In this case, the receiving tape corresponds to the first tape and the cover tape corresponds to the second tape.

The present invention also provides an apparatus for measuring the force required for stripping a second tape, which is adhered to a first tape, from the first tape. This measuring apparatus comprises a drive motor, which rotatably drives a center shaft. The center shaft comprises a main river side bevel gear, which engages with a first follower side bevel gear provided on a forward end portion of a first screw shaft. The driver side bevel gear also engages with a second follower side bevel gear, which is provided on a forward end portion of a second screw shaft. The second screw shaft has the same lead (pitch) as the first screw shaft. The first screw shaft is rotatably supported by a first frame, while the second screw shaft is rotatably supported by a second frame, which is rotatable about the center shaft. Preferably the first frame is also rotatable about the center shaft. The second frame is selectively fixable at an adjustable angle of rotation. A first holder engages with the first screw shaft, and is linearly movably guided along the axial direction of the first screw shaft. The first holder is adapted to support the first tape, after it has been released from the second tape. A second holder engages with the second screw shaft, and is linearly movably guided along the axial direction of the second screw shaft. The second holder is adapted to support the second tape after it has been stripped from the first holder. The second tape is provided with a sensor for detecting the tensile force acting on the second tape.

Preferably the aforementioned apparatus according to the present invention further comprises a first guide which comes into contact with the first tape in a position immediately ahead of the position where the second tape is stripped from the first tape, a second guide which comes into contact with the second tape upstream from the first guide in with respect to the direction of movement of the first and second tapes, and a third guide which comes into contact with the surface of the first tape to which the second tape was adhered after stripping of the second tape from the first tape.

According to the inventive method, the first and second tapes are pulled at the same speed at any prescribed stripping angle to measure the stripping force, by detecting the tensile force currently acting on the second tape. Thus, the stripping force can be measured in with high accuracy and with no variation in the stripping angle during stripping.

Further, the respective forward ends of the first and second tapes may be simply supported during the measurement, and hence it is not necessary to cut off a part of the tape package or fix the overall tape package to a support or the like, dissimilarly to the prior art. Thus, a tape package which is found on a reel or the like can be directly used for the to measurement of the stripping force, whereby the fixing and replacement operation can be simplified to extremely improve the efficiency of the measuring operation.

With the inventive apparatus, the stripping angle can be extremely easily changed by simply rotating the second frame, which supports the second screw shaft, about the center shaft. Further, it is possible to obtain stripping force data from a single tape package at different stripping angles, since the stripping force can be measured continuously with continuous tape package as hereinabove described.

The inventive method can be most simply implemented by the inventive apparatus since one motor can linearly move two tape holders at the same speed to separate the holders from each other through a bevel gear mechanism.

These and other objects, features, aspects and advantages of the present invention will become more apparent from the following detailed description of embodiments of the present invention when taken in conjunction with the accompanying drawings.

DESCRIPTION OF THE PREFERRED EMBODIMENTS

Figure 1:
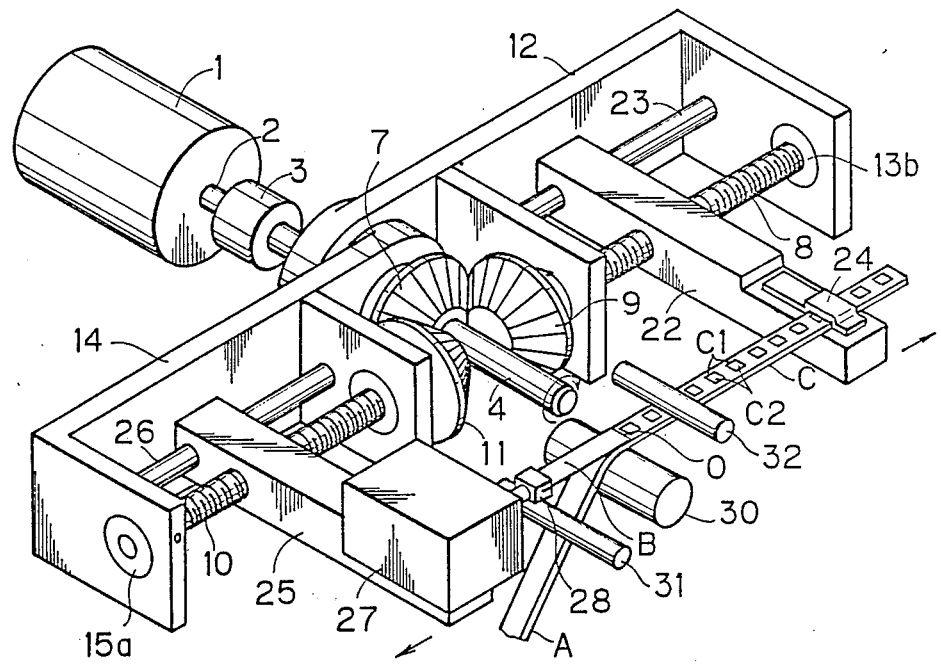
FIG. 1 is a perspective view showing an apparatus for measuring a stripping force according to an embodiment of the present invention, with a fixing member being omitted.
Figure 2:
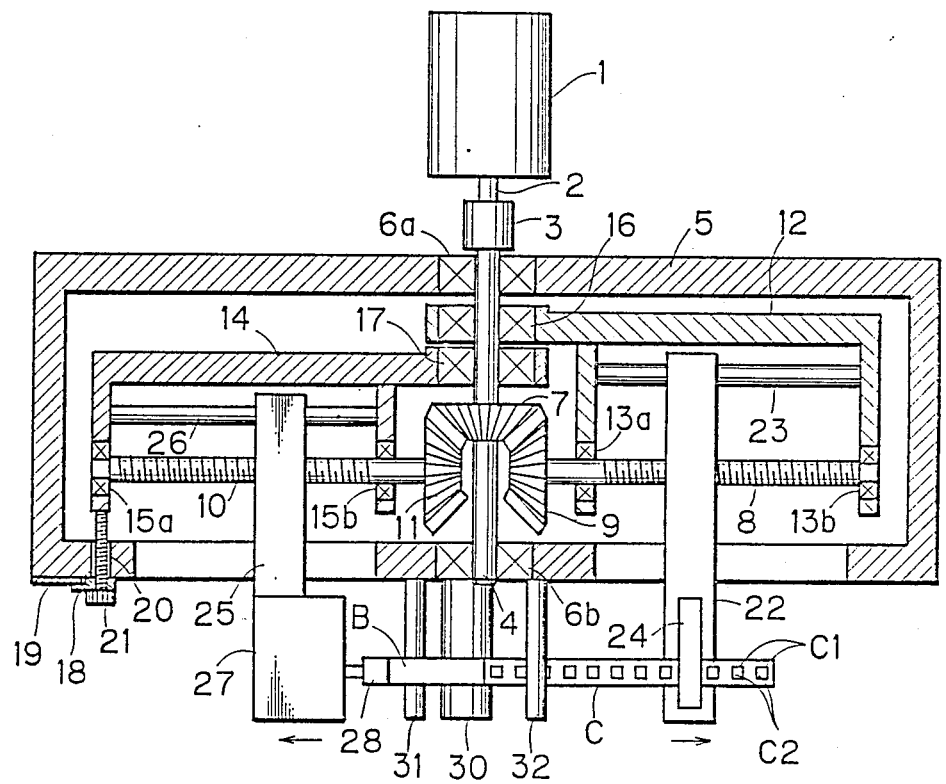
FIG. 2 is a cross-sectional view of the apparatus for measuring a stripping force shown in FIG. 1.
Figure 3:
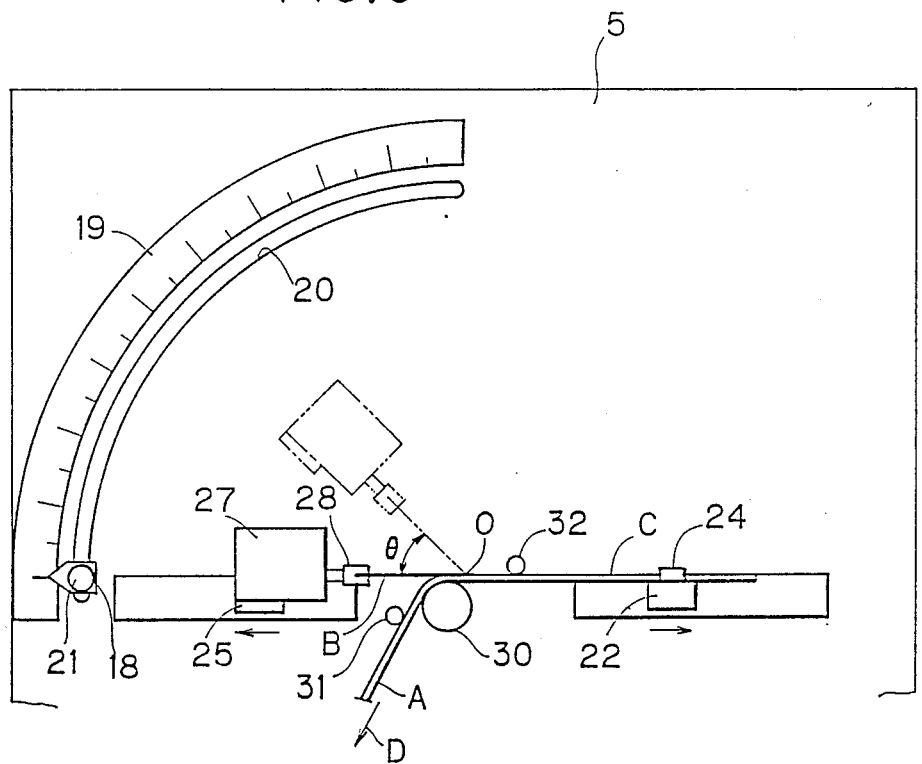
FIG. 3 is a front elevational view of the apparatus for measuring stripping force shown in FIG. 1.

FIGS. 1 to 3 show an apparatus for measuring the required force for stripping an adhered tape according to an embodiment of the present invention.

This embodiment is adapted to measure the force required for stripping a cover tape B which is adhered to a receiving tape C of a tape package A, comprising the receiving tape C and the cover tape B, from the receiving tape C. As shown in FIGS. 1 and 2, the receiving tape C is provided with a plurality of cavities C1 which are distributed along its longitudinal direction for receiving respective components C2 such as chip-type electronic components. As shown, the forward end of the cover tape (second tape) B has been stripped off the tape package A and drawn toward the left (FIG. 2) and clamped in the clamp 28, thus exposing the receiving (first) tape C, a forward end of which has been drawn toward the right, as seen in FIG. 2.

A rotary shaft 2 of a drive motor 1 such as a DC motor is coupled with a center shaft 4 through a coupling 3. Both ends of the center shaft 4 are supported by a fixing member 5 (see FIG. 2) such as a casing, by means of bearings 6a and 6b. A main bevel gear 7 is fixed at an intermediate portion of the center shaft 4, to orthogonally engage with a first bevel gear 9 which is fixed to the forward end of a first screw shaft 8 and a second bevel gear 11 which is fixed to the forward end of a second screw shaft 10.

The first screw shaft 8 is rotatably supported by a first frame 12 by means of bearings 13a and 13b, and the second screw shaft 10 which has the same lead as the first screw shaft 8 is rotatably supported by a second frame 14 by means of bearings 15a and 15b. End portions of the first and second frames 12 and 14 are coupled to the center shaft 4 via bearings 16 and 17 respectively, whereby the frames 12 and 14 are rotatable about the center shaft 4. The fixing member 5 is provided on its front surface with a pointer 18, which is fixed to the second frame 14 by a set screw 21 engaging with the second frame 14 through an arcuate hole 20 (see FIG. 3) defined in the fixing member 5. This pointer 18 is movable along the arcuate hole 20 in response to movement of the second frame 14, while the same can be fixed at an arbitrary position by tightening the set screw 21. An arcuate angle gauge 19 is mounted on the front surface of the fixing member 5 along the locus of movement of the pointer 18. When the pointer 18 is moved along the arcuate hole 20 of the fixing member 5, following the movement of the second frame 14, therefore, the forward end portion of the pointer 18 slides along the divisions of the angle gauge 19. Thus, the second frame 14 can be easily fixed at a desired set angle by reading the division of the angle gauge 19 indicated by the pointer 18.

The first screw shaft 8 engages with a receiving tape holder 22, whose rear end portion slidably engages with a slide shaft 23 which is fixed to the first frame 12 in parallel with the first screw shaft 8. Upon rotation of the first screw shaft 8, therefore, the receiving tape holder 22 is linearly moved along the axial direction of the first screw shaft 8. A clamp 24 is mounted on an upper surface part of the forward end portion of the receiving tape holder 22 frontwardly projecting beyond the fixing member 5, to detachably support the receiving tape C of the tape package A which has been released from the cover tape B. The second screw shaft 10 engages with a cover tape holder 25, whose rear end portion slidably engages with a slide shaft 26 which is fixed to the second frame 14 in parallel with the second screw shaft 10. Thus, the cover tape holder 25 is also linearly moved following rotation of the second screw shaft 10, similarly to the receiving tape holder 22. A tensile force detecting sensor 27 such as a load cell or a strain gauge is fixed to the forward end portion of the cover tape holder 25 frontwardly projecting beyond the fixing member 5, and a clamp 28 is mounted on the sensor 27 to detachably support the forward end portion of the cover tape B.

As hereinabove described, the receiving tape holder 22 and the cover tape holder 25 are linearly moved following rotation of the screw shafts 8 and 10, which are threaded in opposite senses but with the same pitch. Therefore, when the center shaft 4 is rotated in the direction indicated by the arrow shown in FIG. 1, for example, the receiving tape holder 22 and the cover tape holder 25 are moved in opposite directions from each other at the same speed. Thus, the cover tape B and the receiving tape C can be pulled at the same speed.

A guide 30 is arranged in a position slightly offset leftwardly (in FIG. 3) from a separation point O (center of the center shaft 4), in order to support the lower surface of the tape package A, while other guides 31 and 32 are provided in the vicinity of the guide 30 in order to press the upper surface of the unseparated tape package A and that of the receiving tape C which has been released from the cover tape B respectively. The guide 30 is adapted to suppress any vertical fluctuation of the separation point O and the guide 31 is adapted to prevent the tape package A from upward separation and interference with the tensile force detecting sensor 27, while the guide 32 is adapted to prevent upward separation of the receiving tape C.

The inventive method of measuring force for stripping an adhered tape will now be described.

First, the cover tape B is partially stripped from an end of the tape package A. The forward end of the cover tape B is inserted into the clamp 28 of the tensile force detecting sensor 27 and the forward end portion of the receiving tape C is clamped in the clamp 24 of the receiving tape holder 22. The tapes B and C are pulled so as to set the separation point O in alignment with the center of the center shaft 4. Then, the drive motor 1 is driven in the direction of the arrow shown in FIG. 1 to reversely rotate the first and second screw shafts 8 and 10, whereby the holders 22 and 25 are linearly separated from each other at the same speed. Thus, the cover tape B and the receiving tape C are pulled at the same speed, so that the initially set separation point O is retained at the central position of the center shaft 4 with no fluctuation in a stripping angle $\theta$(see FIG. 3). Therefore, the stripping force can be measured in with high accuracy by detecting the tensile force acting on the cover tape B during the stripping operation by means of the sensor 27.

The stripping angle $\theta$ may be simply changed by loosening the set screw 21 and rotating the second frame 14 about the center shaft 4, and then tightening the set screw 21 at the position of a desired angle. In other words, the second frame 14 may be rotated to integrally rotate the tensile force detecting sensor 27, thereby to arbitrarily adjust the stripping angle $\theta$ as shown by phantom lines in FIG. 3. The bevel gears 7 and 11 will not be disengaged at this time since the second frame 14 is rotated about the center shaft 4.

When the cover tape B is stripped with the stripping angle shown by the phantom lines in FIG. 3, a portion of the tape package A or receiving tape C located between the guides 31 and 32 may be undesirably separated upwardly from the guide 30. However, such upward separation of the tape package A or receiving tape C can be sufficiently prevented by the rigidity of the receiving tape C, which is formed of a cardboard material, for example, by reducing the distances between the guides 30, 31 and 32. In order to further positively prevent such upward separation, a proper tensile force may be applied to the tape package A in a direction D shown in FIG. 3, for example.

The present invention is not restricted to the above embodiment, but the following modifications are also available:

For example, the first frame 12 may be integral with the fixing member 5. However, the structure of the embodiment shown in FIG. 1 is particularly effective in that the degree of freedom for setting the stripping angle is increased, since not only the second frame 14 but also the first frame 12 is supported rotatably about the center shaft 4.

The conical bevel gears 7, 9 and 11 shown in the embodiment may be replaced by face gears, as long as the gear mechanism transfers power from the center shaft 4 to the orthogonal screw shafts 8 and 10. It is noted that the first and second bevel gears 9 and 11 must be formed by gears of the same items pitch characteristics.

The slide shafts 23 and 26 may be replaced by rails etc. which are provided on the frames 12 and 14 as means for linearly movably guiding the receiving tape holder 22 and the cover tape holder 25.

Further, the mechanism for moving the receiving tape holder 22 and the cover tape holder 25 is not restricted to the slidable screw mechanism shown in the embodiment, but may be implemented by a ball screw mechanism which has small frictional resistance and excellent positional accuracy.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of measuring a force required for stripping a second tape adhered to a first tape from said first tape, comprising the steps of:
   stripping an initial portion of said second tape from a corresponding initial portion of said first tape;
   bending said second tape portion to form a prescribed stripping angle with respect to said initial portion of said second tape;
   moving said portion of said first tape released from said second tape and said portion of said second tape stripped from said first tape in opposite directions from each other at the same speed along loci of linear movement respectively while maintaining said stripping angle substantially constant; and
   measuring a tensile force acting on said second tape during said movement thereby to determine the force required for stripping said second tape from said first tape.

2. A method in accordance with claim 1, wherein said loci of said linear movement of said released portion of said first tape and said stripped portion of said second tape are located on the same straight line in said step of moving said released portion of said first tape and said stripped portion of said second tape in opposite directions from each other.

3. A method in accordance with claim 1, wherein said first tape is a receiving tape provided with a plurality of cavities distributed along its longitudinal direction for receiving components, and said second tape is a cover tape adhered to said receiving tape for closing said cavities.

4. A method in accordance with claim 1, wherein said second tape is stripped from said first tape at a stripping point, and said stripping point substantially does not move during said moving step.

5. A method in accordance with claim 4, comprising guiding said tapes slightly upstream from said stripping point prior to said stripping, by a first guide which engages a lower side of said tapes.

6. A method in accordance with claim 5, comprising guiding said tapes by a second guide engaging an upper side thereof, upstream from said first guide.

7. A method in accordance with claim 5, comprising guiding said first tape by a third guide engaging an upper side thereof, downstream from said first guide.

8. A method in accordance with claim 5, further comprising substantially suppressing any movement of said tapes away from said first guide and any movement of said stripping point not in the direction of movement of said tapes.

9. A method in accordance with claim 1, wherein said stripping angle is adjusted by moving said initial portion of said second tape from an initial position.

10. A method in accordance with claim 9, wherein said stripping angle is also adjusted by moving said initial portion of said first tape from an initial position.

11. An apparatus for measuring a force required for stripping a second tape adhered to a first tape from said first tape, comprising:
a drive motor;
a center shaft rotatably driven by said drive motor and having a main driver side bevel gear;
a first screw shaft provided on a forward end portion thereof with a first follower side bevel gear engaging with said driver side bevel gear;
a second screw shaft provided on a forward end portion thereof with a second follower side bevel gear engaging with said driver side bevel gear and having the same pitch as said first screw shaft but threaded in the opposite direction;
a first frame rotatably supporting said first screw shaft;
a second frame rotatably supporting said second screw shaft;
a first holder engaging with said first screw shaft and being linearly movably guided along the axial direction of said first screw shaft and having means for holding an end of said first tape released from said second tape;
a second holder engaging with said second screw shaft and being linearly movably guided along the axial direction of said second screw shaft and having means for holding an end of said second tape stripped from said first tape;
whereby rotation of said center shaft by said drive motor causes said ends of said first and second tapes to be moved apart by movement of said first and second holders; and
a sensor associated with at least one of said holders which detects a tensile force acting on at least one of said tapes.

12. An apparatus in accordance with claim 11, further comprising a first guide means for contacting said first tape at a position immediately upstream from a point where said second tape is stripped from said first tape, a second guide means for contacting said second tape upstream from said first guide with respect to the direction of movement of said first and second tapes, and a third guide means for contacting a surface of said first tape to which said second tape was adhered, after said second tape has been stripped from said first tape.

13. An apparatus in accordance with claim 11, wherein said second frame is rotatable about said center shaft for setting a stripping angle defined between said second frame and said first frame; and
further comprising means for selectively fixing said second frame at an adjustable angle of rotation about said center shaft;
whereby said respective linear movements of said first and second holders also define said stripping angle; and
whereby said apparatus can measure said tensile force at any said adjustable stripping angle.

14. An apparatus in accordance with claim 13, wherein said means for selectively fixing said second frame at said adjustable angle of rotation comprises a set screw engaging with said second frame and a fixing member having an arcuate hole for receiving said set screw and engaging with said set screw by tightening of said set screw.

15. An apparatus in accordance with claim 14, further comprising a pointer movable with said set screw and an angle gauge provided on said fixing member for indicating an angle in relation to said pointer.

16. An apparatus in accordance with claim 13, wherein said first frame is also rotatable about said center shaft for further setting said stripping angle.

17. An apparatus in accordance with claim 11, wherein said movement of said holders strips said second tape from said first tape at a stripping point, and said stripping point substantially does not move during said stripping.

18. An apparatus in accordance with claim 17, wherein said stripping point is substantially along the long axis of said center shaft.

19. An apparatus in accordance with claim 11, further comprising first guide means engaging a lower side of said tapes for guiding said tapes slightly upstream from said stripping point prior to said stripping.

20. An apparatus in accordance with claim 19, further comprising second guide means engaging an upper side of said tapes upstream from said first guide, for further guiding said tapes.

21. An apparatus in accordance with claim 19, further comprising third guide means engaging an upper side of said first tape downstream from said first guide, for further guiding said first tape.

22. An apparatus in accordance with claim 19, comprising means for substantially suppressing any movement of said tapes away from said first guide means and any movement of said stripping point not in the direction of movement of said tapes.

23. An apparatus in accordance with claim 11, wherein said stripping angle is adjustable by moving said initial portion of said second tape from an initial position.

24. An apparatus in accordance with claim 23, wherein said stripping angle is further adjustable by moving said initial portion of said first tape from an initial position.

25. An apparatus for measuring a force required for stripping a second tape adhered to a first tape from said first tape, comprising:
drive means;
center shaft means rotatably driven by said drive means;
a first holder having means for holding an end of said first tape released from said second tape;
a second holder having means for holding an end of said second tape stripped from said first tape;

means responsive to rotation of said center shaft means by said drive means for causing said ends of said first and second tapes to be moved apart by opposite movement of said first and second holders; and sensor means associated with at least one of said holders which detects a tensile force acting on at least one of said tapes.

26. An apparatus in accordance with claim 25, further comprising:

main driver side gear means rotatable in response to said center shaft means;

first screw shaft means having first follower side gear means engaging with said driver side gear means and having thread means thereon which define a thread pitch;

second screw shaft means having second follower side gear means engaging with said driver side gear means and having thread means thereon defining the same pitch as said thread means of said first screw shaft means but threaded in the opposite direction;

a first frame rotatably supporting said first screw shaft means;

a second frame rotatably supporting said second screw shaft means;

wherein said first holder engages with said first screw shaft means and is linearly movably guided along the axial direction of said first screw shaft means; and wherein said second holder engages with said second screw shaft means and is linearly movably guided along the axial direction of said second screw shaft means.

* * * * *